(12) United States Patent
van de Pasch et al.

(10) Patent No.: US 6,392,738 B1
(45) Date of Patent: May 21, 2002

(54) LITHOGRAPHIC PROJECTION APPARATUS

(75) Inventors: Engelbertus A. F. van de Pasch, Oirschot; Aschwin L. H. J. van Meer, Roosendaal; Franciscus A. G. Klaassen, Best, all of (NL)

(73) Assignee: ASML Netherlands B.V., Veldhoven (NL)

(*) Notice: Subject to any disclaimer, the term of this patent is extended or adjusted under 35 U.S.C. 154(b) by 0 days.

(21) Appl. No.: 09/684,959

(22) Filed: Oct. 10, 2000

(30) Foreign Application Priority Data

Oct. 12, 1999 (EP) .............................. 99203327

(51) Int. Cl.[7] .................. G03B 27/52; G03B 27/42; G03B 27/54; G01N 1/10
(52) U.S. Cl. ................ 355/30; 355/53; 355/67
(58) Field of Search .............. 355/30, 53, 67–69, 355/72–76; 356/237.2–237.5; 250/559.4, 559.41

(56) References Cited

U.S. PATENT DOCUMENTS

| | | | | |
|---|---|---|---|---|
| RE33,991 E | * | 7/1992 | Shiba et al. | ............... 356/237 |
| 5,539,514 A | * | 7/1996 | Shishido et al. | ............. 356/237 |
| 5,559,582 A | * | 9/1996 | Nishi et al. | ..................... 355/30 |
| 5,673,208 A | | 9/1997 | Meier et al. | ................. 364/525 |
| 5,821,175 A | * | 10/1998 | Engelsberg | ................. 438/795 |
| 5,825,470 A | * | 10/1998 | Miyai et al. | .................... 355/72 |
| 5,898,182 A | | 4/1999 | Toyama | ................. 250/559.41 |
| 6,038,015 A | | 3/2000 | Kawata | ....................... 355/67 |

* cited by examiner

Primary Examiner—Russell Adams
Assistant Examiner—Henry Hung Nguyen
(74) Attorney, Agent, or Firm—Pillsbury Winthrop LLP

(57) ABSTRACT

A lithographic projection apparatus is disclosed. The lithographic projection apparatus includes an illumination system to supply a projection beam of radiation, a first object table to hold a mask, a second object table provided with a support surface to support and hold a substrate at its backside surface and a projection system to image an irradiated portion of the mask onto a target portion of the substrate including a detector constructed and arranged to detect the presence of contamination on one or both of the support surface and the substrate backside surface.

14 Claims, 5 Drawing Sheets

LITHOGRAPHIC PROJECTION APPARATUS

BACKGROUND OF THE INVENTION

1. Field of the Invention

The present invention relates to contamination detection means. More particularly, the invention relates to contamination detection means in a lithographic projection apparatus comprising:

- an illumination system for supplying a projection beam of radiation;
- a first object table for holding a mask;
- a second object table provided with a support surface for supporting and holding a substrate at its backside surface; and
- a projection system for imaging an irradiated portion of the mask onto a target portion of the substrate.

2. Description of the Related Art

An apparatus of this type can be used, for example, in the manufacture of integrated circuits (ICs). In such a case, the mask (reticle) may contain a circuit pattern corresponding to an individual layer of the IC, and this pattern can then be imaged onto a target portion comprising one or more dies on a substrate (silicon wafer) that has been coated with a layer of radiation sensitive material (resist) on its top surface. In general, a single wafer will contain a whole network of adjacent target portions that are successively irradiated through the reticle, one at a time. In one type of lithographic projection apparatus, each target portion is irradiated by exposing the entire reticle pattern onto the target portion at once; such an apparatus is commonly referred to as a waferstepper. In an alternative apparatus—which is commonly referred to as a step-and-scan apparatus—each target portion is irradiated by progressively scanning the reticle pattern under the projection beam in a given reference direction (the "scanning" direction) while synchronously scanning the wafer table parallel or anti-parallel to this direction; since, in general, the projection system will have a magnification factor M (generally <1), the speed v at which the wafer table is scanned will be a factor M times that at which the reticle table is scanned. More information with regard to lithographic devices as here described can be gleaned from International Patent Application WO 97/33205.

In general, apparatus of this type contained a single first object (mask) table and a single second object (substrate) table. However, machines are becoming available in which there are at least two independently movable substrate tables; see, for example, the multi-stage apparatus described in International Patent Applications WO 98/28665 and WO 98/40791. The basic operating principle behind such multi-stage apparatus is that, while a first substrate table is underneath the projection system so as to allow exposure of a first substrate located on that table, a second substrate table can run to a loading position, discharge an exposed substrate, pick up a new substrate, perform some initial metrology steps on the new substrate, and then stand by to transfer this new substrate to the exposure position underneath the projection system as soon as exposure of the first substrate is completed, whence the cycle repeats itself; in this manner, it is possible to achieve a substantially increased machine throughput, which in turn improves the cost of ownership of the machine.

Lithographic apparatus may employ various types of projection radiation, such as ultra-violet light (UV), extreme UV, X-rays, ion beams or electron beams, for example. Depending on the type of radiation used and the particular design requirements of the apparatus, the projection system may be refractive, reflective or catadioptric, for example, and may comprise vitreous components, grazing-incidence mirrors, selective multi-layer coatings, magnetic and/or electrostatic field lenses, etc; for simplicity, such components may be loosely referred to in this text, either singly or collectively, as a "lens". The apparatus may comprise components that are operated in vacuum, and are correspondingly vacuum-compatible.

When a substrate is loaded onto the support surface of the substrate table, the substrate may be sucked against the support surface applying a vacuum to a space between the support surface and the backside surface of the substrate. Using this method the substrate will take a form determined by the support surface. The support surface may be provided with a matrix arrangement of protrusions, substantially perpendicular to the support surface whereby the backside of the substrate is lying on a contact surface represented by a top part of the protrusions. The form of the substrate will then be determined by the contact surfaces that are all located in the same plane. If contamination particles are present in between the support surface and the backside surface of the substrate the form of the substrate is not determined only by the form of the support surface but also by the contamination particles. The contamination could cause an unacceptable deformation of the substrate, which may result in focus and overlay errors during imaging of the pattern in the mask onto a top surface of the substrate. The errors may result in a rejection of manufactured substrates and thus in a lower throughput of the lithographic apparatus, which leads to an increase in the cost of ownership.

SUMMARY OF THE INVENTION

It is an object of the invention to prevent focus and overlay errors caused by contamination particles present in between the support surface and the substrate backside surface. These and other objects are achieved in an apparatus as specified in the opening paragraph, characterized in that the apparatus comprises contamination detection means constructed and arranged to detect the presence of contamination on one or both of the support surface and the substrate backside surface.

By detecting the presence of contamination on the support surface one may initiate cleaning of the support surface such that focus and overlay errors caused by said contamination are anticipated. By detecting the presence of contamination on the backside surface of the substrate one may choose to reject contaminated substrates such that the contamination will not reach the support surface. In both manners fewer manufactured substrates will be rejected and the cost of ownership of the apparatus will be improved.

In a first embodiment of the invention, said contamination detection means comprises:

- level sensing means constructed and arranged to detect a surface figure of a substrate positioned upon said support surface;
- data storage means for storing surface figures of at least two substrates; and
- processing means adapted to compare surface figures of at least two substrates stored in said data storage means so as to recognize a recurring deformation in the surface figures of said substrates at a similar location indicating the presence of contamination at that location on the support surface.

In this way level sensing means already present in the apparatus may be used for the detection of contamination present at the support surface. Such level sensing means may detect the surface figure of a substrate positioned upon said support surface and said surface figure may be used during exposure to adjust the height and tilt of the substrate such that the substrate will be positioned within the focal plane of the projection system. In case the surface figure of more than one substrate comprises a deformation at a similar location, said deformation indicates contamination of the support surface on said location because said contamination will deform every substrate positioned upon that support surface.

In a further embodiment of the invention, the contamination detection means is adapted to detect a location of contamination on said support surface and said apparatus comprises a cleaning tool adapted to move with respect to said support surface to said location and to clean said location. In this manner contamination detected on a particular location on said support surface may be cleaned in situ by the cleaning tool and a throughput penalty is avoided because opening, inspecting, cleaning and closing of the apparatus, which may cost a lot of time in which the apparatus is not operative, is prevented. In-situ cleaning of a particular contaminated location has. the further advantage that it is not necessary to clean the whole support surface, causing wear of the cleaning tool and of the support surface.

In yet a further embodiment the cleaning tool comprises a cleaning block having a cleaning surface and is further constructed and arranged to be positioned with its cleaning surface against said support surface and to be movable with respect to and in a plane parallel to the support surface when positioned against said support surface. Such a cleaning tool is very effective in removing contamination by abrasive cleaning of the support surface. The cleaning tool and the second object table may be constructed and arranged such that the support surface is moved and the cleaning block is held stationary against the contaminated location or such that the cleaning block is moved while the second object table is held stationary. It may also be advantageous to move both the second object table and the cleaning block. The cleaning block may comprise a ceramic material, for example, alumina and titanium oxide. The cleaning block may be at least partially electrically conductive, such that a static electrical charge will not accumulate upon the cleaning block and support surface. Attraction caused by such an electrical charge between the support surface and the cleaning block will then not occur. The roughness of the cleaning surface is advantageously 0.1 $\mu$m or less. The roughness is defined as the mean value of the absolute distances between the actual surface figure of the cleaning surface and the average surface figure of the cleaning surface. Such a roughness will be enough for cleaning of the contamination but will not damage the support surface.

In still a further embodiment of the invention the cleaning block comprises a sponge. It may be advantageous that said sponge is constructed and arranged to be provided with a solvent, for example acetone. The sponge may be made from polyvinyl alcohol, for example. The contaminants present on the support surface may be dissolved in the solvent and absorbed by the sponge.

In another embodiment according to the invention said cleaning tool comprises a source of radiation and radiation directing means for directing said radiation upon said support surface to crack contaminants present on the support surface. For this purpose a laser or a lamp radiating ultraviolet radiation can be used. The embodiment may be provided with purge gas means for supplying a purge gas over said support surface. The purge gas, for example an inert gas, will prevent re-contamination of the support surface and will remove the contaminants from the apparatus.

In yet another embodiment the contamination detection means comprises a substrate inspection tool constructed and arranged to inspect the backside surface of the substrate for contamination and to reject a contaminated substrate from being loaded onto the support surface. A contaminated substrate may thus be prevented from entering the (imaging part of the) lithographic apparatus. Associated contamination will not be allowed to come into contact with and remain on the support surface. The substrate may than be taken out of the process to be discarded or cleaned elsewhere.

The inspection tool may comprise a radiation source generating a beam of electromagnetic radiation, means constructed and arranged to scan the radiation beam over the backside of the substrate, and a detector constructed and arranged to detect radiation which is off-specularly scattered by contamination present on said backside. Such an inspection tool is very efficient and fast in detecting any contamination particles present on the backside surface of the substrate.

The invention also relates to a device manufacturing method comprising the steps of:
 providing a substrate which is at least partially covered by a layer of radiation-sensitive material to a substrate table provided with a support surface for holding and supporting the substrate at its backside surface;
 providing a mask which contains a pattern; and
 using a projection beam of radiation to project an image of at least a portion of the mask pattern via a projection system onto a target portion of the layer of radiation-sensitive material,
characterized in that the method further comprises the step of detecting the presence of contamination on one or both of the support surface and the substrate backside surface.

In a manufacturing process using a lithographic projection apparatus, a pattern in a mask is imaged onto a substrate which is at least partially covered by a layer of radiation sensitive material (resist). Prior to this imaging step, the substrate may undergo various procedures, such as priming, resist coating and a soft bake. After exposure, the substrate may be subjected to other procedures, such as a post-exposure bake (PEB), development, a hard bake and measurement/inspection of the imaged features. This array of procedures is used as a basis to pattern an individual layer of a device, e.g. an IC. Such a patterned layer may then undergo various processes such as etching, ion-implantation (doping), metallization, oxidation, chemo-mechanical polishing, etc., all intended to finish off an individual layer. If several layers are required, then the whole procedure, or a variant thereof, will have to be repeated for each new layer. Eventually, an array of devices will be present on the substrate (wafer). These devices are then separated from one another by a technique such as dicing or sawing, whence the individual devices can be mounted on a carrier, connected to pins, etc. Further information regarding such processes can be obtained, for example, from the book "Microchip Fabrication: A Practical Guide to Semiconductor Processing", Third Edition, by Peter van Zant, McGraw Hill Publishing Co., 1997, ISBN 0-07-067250-4.

Although specific reference has been made hereabove to the use of the apparatus according to the invention in the manufacture of ICs, it should be explicitly understood that such an apparatus has many other possible applications. For example, it may be employed in the manufacture of integrated optical systems, guidance and detection patterns for magnetic domain memories, liquid-crystal display panels, thin-film magnetic heads, etc. The skilled artisan will appreciate that, in the context of such alternative applications, any use of the terms "reticle", "wafer" or "die" in this text should be considered as being replaced by the more general terms "mask", "substrate" and "target portion", respectively.

BRIEF DESCRIPTION OF THE DRAWINGS

The invention and its attendant advantages will be further elucidated with the aid of exemplary Embodiments and the accompanying schematic drawings, wherein.

DETAILED DESCRIPTION OF THE INVENTION

Embodiment 1

Figure 1:
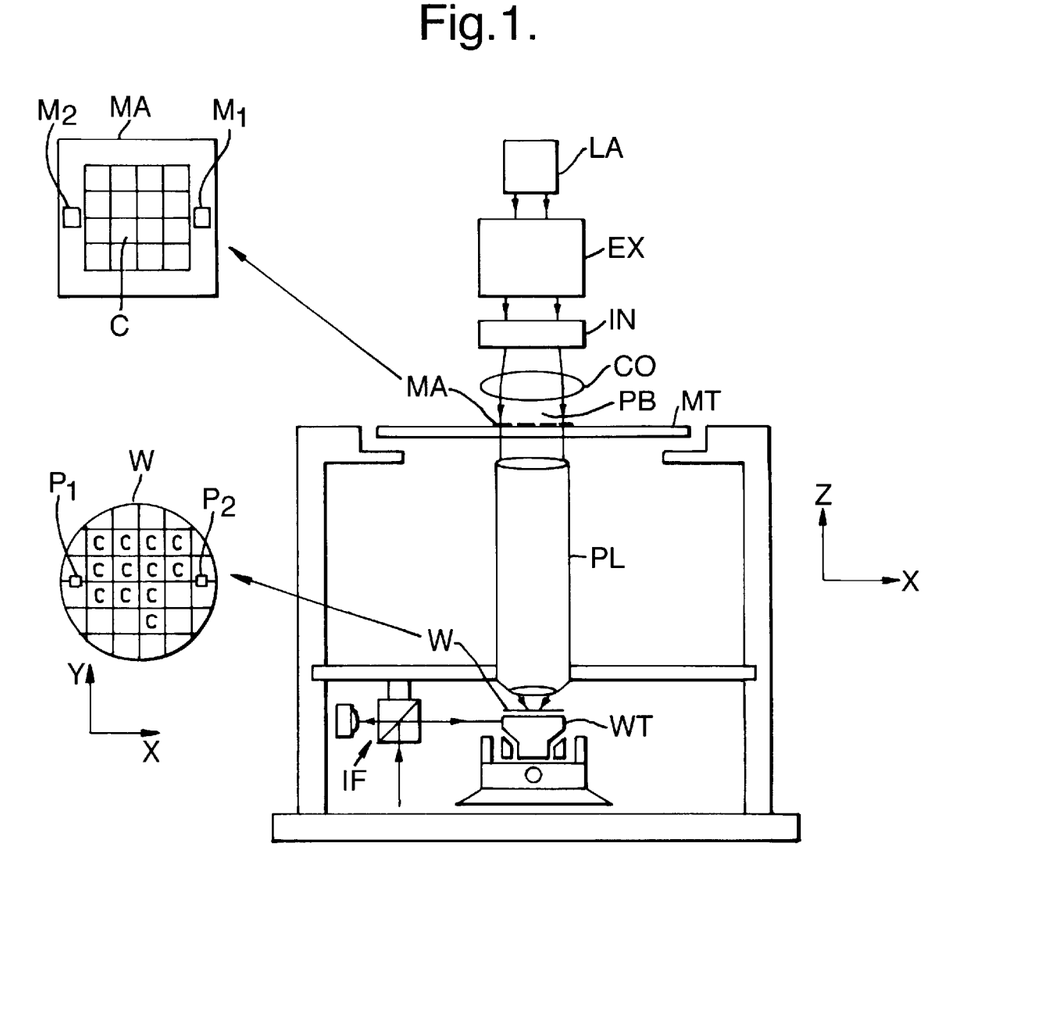
FIG. 1 schematically depicts a lithographic projection apparatus suitable for implementation of the present invention.

FIG. 1 schematically depicts a lithographic projection apparatus suitable for implementation of the invention. The apparatus comprises:

- a radiation system LA, Ex, IN, CO for supplying a projection beam PB of radiation (e.g. UV or EUV radiation, X-ray, ions, or electrons);
- a first object table (mask table) MT provided with a mask holder for holding a mask MA (e.g. a reticle);
- a second object table (substrate table) WT provided with a support surface for holding a substrate W (e.g. a resist-coated silicon wafer) at its backside surface; and
- a projection system PL (e.g. a lens or catadioptric system, or a mirror group) for imaging an irradiated portion of the mask MA onto a target portion C of the substrate W.

In this case, the depicted apparatus comprises refractive components.

However, it may alternatively comprise one or more reflective components.

The radiation system comprises a source LA (e.g. a Hg lamp or excimer laser, a thermionic gun or ion source, or a wiggler/undulator situated around the path of an electron beam in a storage ring or synchrotron) which produces a beam of radiation. This beam is passed along various optical components,—e.g. beam shaping optics Ex, an integrator IN and a condenser CO—so that the resultant beam PB has the desired shape and intensity distribution throughout its cross-section.

The beam PB subsequently intercepts the mask MA which is held in a mask holder on a mask table MT. Having passed through the mask MA, the beam PB passes through the projection system PL, which focuses the beam PB onto a target portion C of the substrate W. With the aid of the interferometric displacement and measuring means IF, the substrate table WT can be moved accurately, e.g. so as to position different target portions C in the path of the beam PB.

The depicted apparatus can be used in two different modes:

- In step mode, the mask table MT is kept essentially stationary, and an entire mask image is projected at once (i.e. a single "flash") onto a target portion C. The substrate table WT is then shifted in the x and/or y directions so that a different target portion C can be irradiated by the (stationary) beam PB;
- In scan mode, essentially the same scenario applies, except that a given target portion C is not exposed in a single "flash". Instead, the mask table MT is movable in a given direction (the so-called "scan direction", e.g. the x direction) with a speed v, so that the projection beam PB is caused to scan over a mask image; concurrently, the substrate table WT is simultaneously moved in the same or opposite direction at a speed $V=Mv$, in which M is the magnification of the projection system PL (typically, $M=¼$ or $⅕$). In this manner, a relatively large target portion C can be exposed, without having to compromise on resolution.

Figure 2:
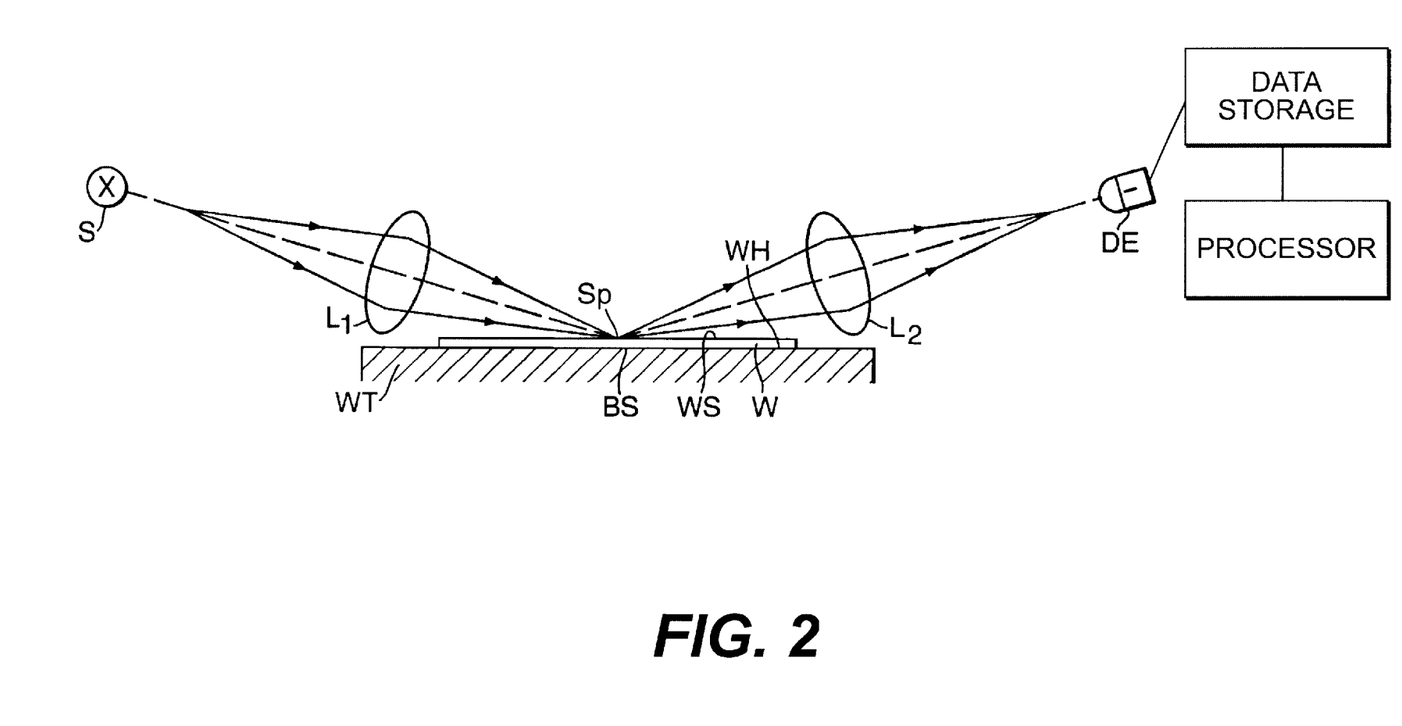
FIG. 2 schematically depicts contamination detection means according to a first embodiment of the invention.

FIG. 2 shows a side-view of the substrate table WT of FIG. 1, and the contamination detection means according to a first embodiment of the invention. Said contamination detection means is provided with level sensing means comprising a source of radiation S, a lens system L1, L2 and a detector DE. The level sensing means is used to detect a surface figure of the top surface WS of a substrate W held with its backside BS on a support surface WH of a substrate table WT. When the level sensing means is used the source of radiation S produces a beam of radiation which is directed with a lens L1 into a spot SP reflected at the top surface WS of the substrate W and subsequently directed through the lens L2 to the detector DE. The detector is constructed and arranged to measure a change in the direction of the beam, indicating a deformation of the surface figure of the top surface WS of the substrate W. Such a deformation may be caused by the substrate W being thicker at a particular location or by contaminants present between the backside surface BS of the substrate W and the support surface WH. By storing the surface figures of at least two substrates in data storage means and by comparing those surface figures, a recurring deformation in the surface figures at a similar location can be detected. This will indicate a contamination of the support surface WH at said location. The level sensing means may be a focus detection system as described in U.S. Pat. No. 5,191,200 which is incorporated herein by reference.

Figure 3A:
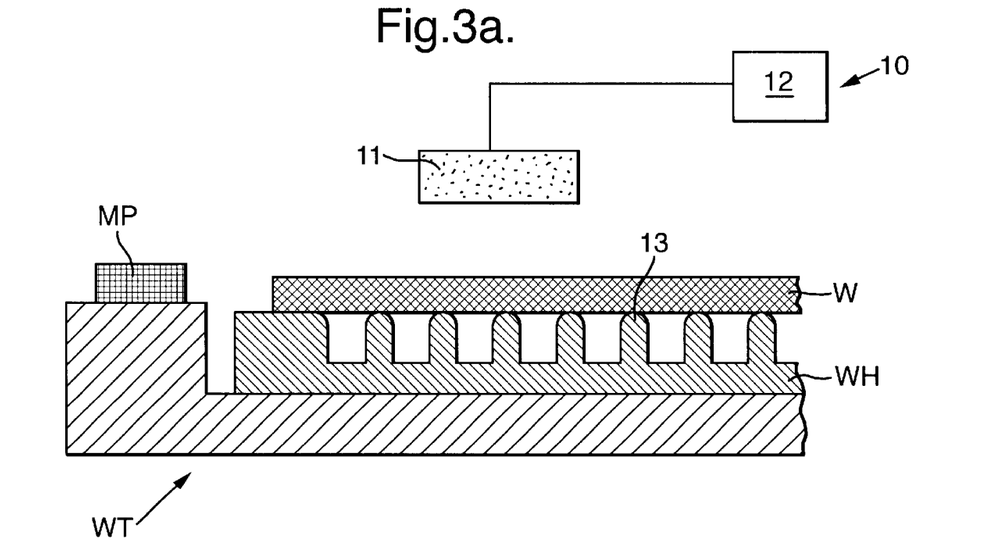
FIGS. 3a and 3b schematically depict a cleaning tool according to the first embodiment of the invention.

FIG. 3a partly shows in cross-section the substrate table WT of FIG. 1 and a substrate table cleaning tool 10 according to the first embodiment of the invention. The substrate table WT is provided with a support surface WH comprising a matrix arrangement of protrusions 13 substantially perpendicular to that surface. A vacuum is created in the region in between the various protrusions 13 and the backside of the substrate W for holding the substrate W on the support surface WH. A contamination particle present in between a protrusion 13 and the backside surface of the substrate W will cause a deformation of the substrate W and thus of its top surface on which a pattern is to be imaged. The protrusions 13 exhibit a relatively small contact surface to the backside surface of the substrate W, resulting in a low probability of contamination being present in between the support surface WH and the substrate W. Another advantage of a relatively small contact surface is that the pressure from the backside surface on the contact surface is relatively high compared to when a larger contact surface is used. The higher pressure may crush any contamination present on the support surface.

Figure 3B:
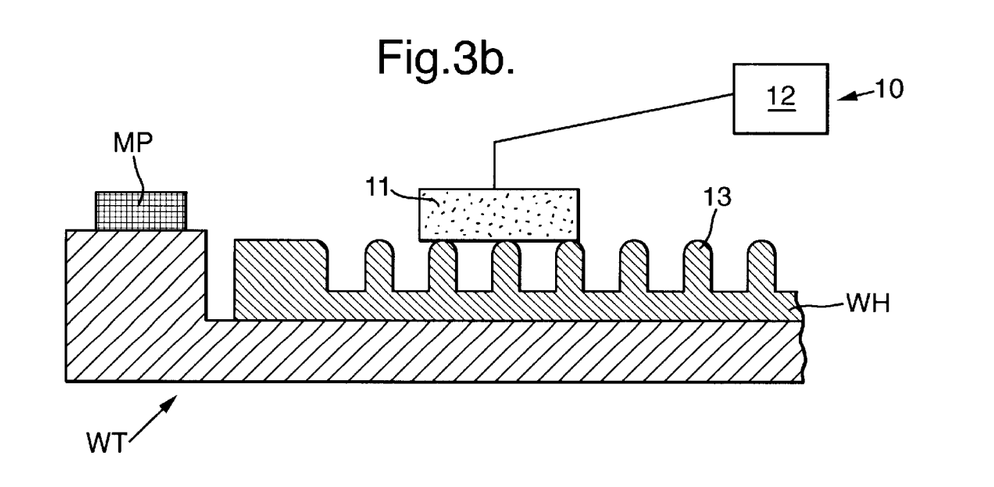

The support surface WH may be cleaned in between unloading of a substrate from and loading of another substrate W onto the substrate table WT when contamination present on the support surface WH is detected. During cleaning of the support surface WH a cleaning block 11 of the wafer holder cleaning tool 10 is lowered onto the protrusions 13 of the support surface WH by a cleaning block drive unit 12, as is shown in FIG. 3b. Subsequently, either the cleaning block 10 or the wafer table WT (or both) will be translated such that the cleaning block 11 moves over the support surface WH. Contamination present on one or more of the protrusions 13 will be wiped off by abrasive cleaning. The cleaning operation may be automated and is performed without opening the lithographic apparatus, which will considerably lower the down time and considerably increase the throughput of the apparatus.

The cleaning block 11 of the embodiment shown comprises a ceramic material which is electrically conductive, such as, for instance, alumina or titanium oxide having a metal as an additive. The cleaning block 11 is electrically connected to ground potential to prevent the build up of an electrostatic charge during the cleaning operation. Such a build up of electrostatic charge may cause an electrostatic attraction between the support surface WH and the cleaning block 11.

Further, the cleaning surface of the cleaning block 11 has a surface roughness in the order of 0.1 µm or less to equally distribute the contact force exerted by the cleaning block 11 over the various protrusions 13 which are in contact with the cleaning block 11, and to prevent an excessive force being exerted on a single protrusion. Such an excessive force could damage a protrusion 13 and therefore damage the evenness of the contact surface presented by the top parts of the protrusions.

FIGS. 3a and 3b show a marker plate MP present on the topside of the substrate table WT next to the protrusions of the support surface WH. The marker incorporated in the marker plate MP is used for an alignment procedure for the substrate W and substrate table WT in the lithographic apparatus. The topside of the marker plate MP is about in the same plane as the topside of a substrate W present on the substrate table WT. During a cleaning operation of the protrusions of the support surface, in which case the substrate W is absent as is shown in FIG. 3b, the cleaning block 11 may run into the marker plate MP or any other further tool which may be present on the topside of the substrate table WT. To prevent the marker plate MP from being damaged the cleaning tool 10 is constructed such that the cleaning block 11 is retracted from the protrusions when a preset value of a force exerted on the marker plate MP or any other tool it may run into is exceeded.

Embodiment 2

Figure 3C:
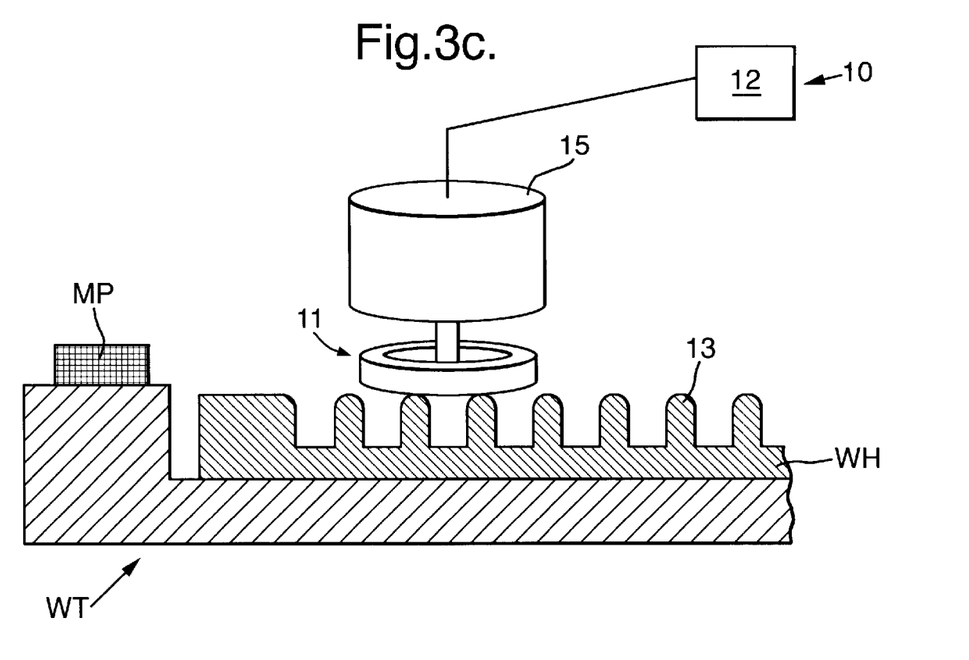
FIG. 3c schematically depicts a substrate cleaning tool according to a second embodiment of the invention.

FIG. 3c shows a cleaning tool 10 according to a second embodiment of the invention for use in the apparatus of FIG. 1. The second embodiment utilizes the contamination detection means of the present invention described above, together with certain refinements to the cleaning tool described below. In the cleaning tool 10 the rotation unit 15 may rotate the cleaning block 11 such that by the rotary movement of the cleaning block 11 abrasive cleaning of the support surface WH occurs. The cleaning block driving unit 12 may be used to locate the cleaning block 11 at a particular location on the support surface WH. Abrasive cleaning will be improved by the rotary movement of the cleaning block 11.

Embodiment 3

Figure 3D:
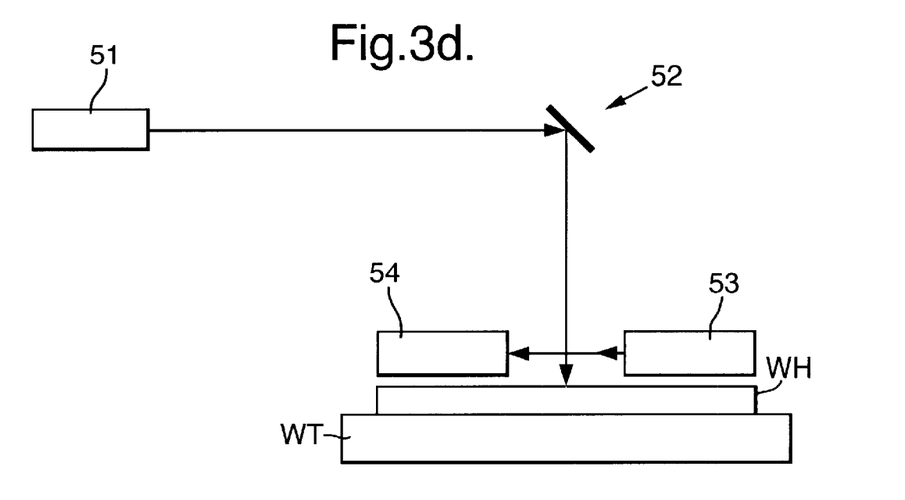
FIG. 3d schematically depicts a substrate cleaning tool according to a third embodiment of the invention; and, FIGS. 4a, 4b and 4c schematically depict contamination detection means according to a fourth embodiment of the invention.

FIG. 3d shows a cleaning tool according to a third embodiment of the invention for use in the apparatus of FIG. 1. The third embodiment utilizes the contamination detection means of the present invention described above. The cleaning tool comprises a source of electromagnetic radiation 51 which radiates a beam of radiation to the mirror 52 which directs the beam of radiation to the support surface WH. By moving the mirror 52 the beam can be moved over the total support surface WH and may be directed to a contamination particle. When the contamination particle is hit it may be evaporated or burned. The cleaning tool may be provided with purge gas means 53, 54 for supplying a purge gas over said main surface to prevent recontamination and to remove contaminant parts.

Embodiment 4

Figure 4A:
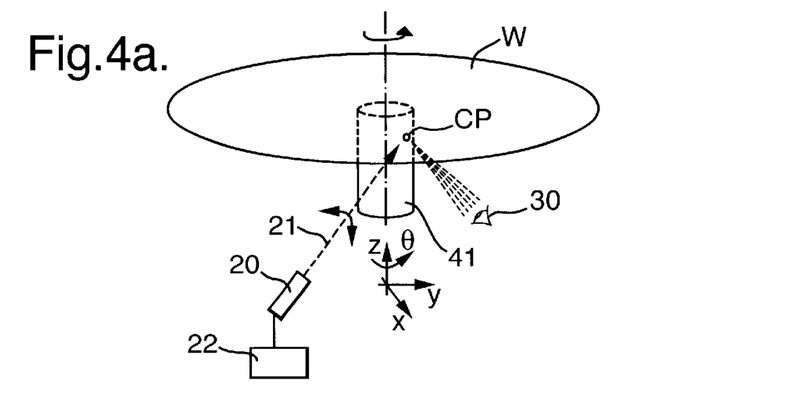
Figure 4B:
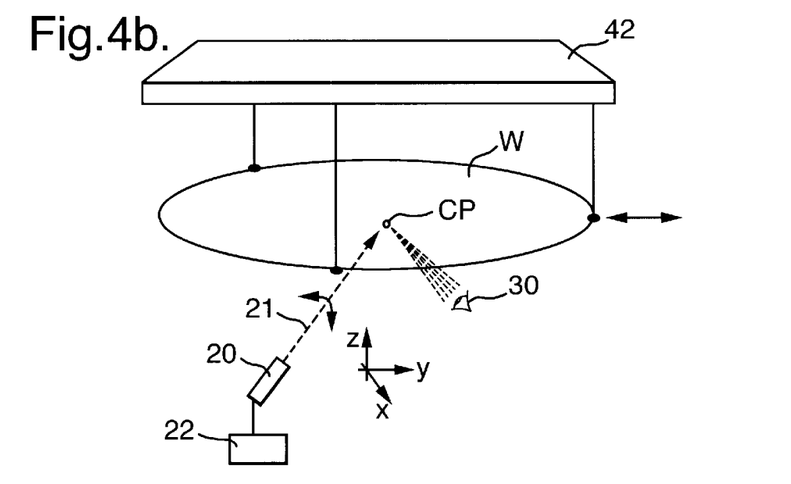
Figure 4C:
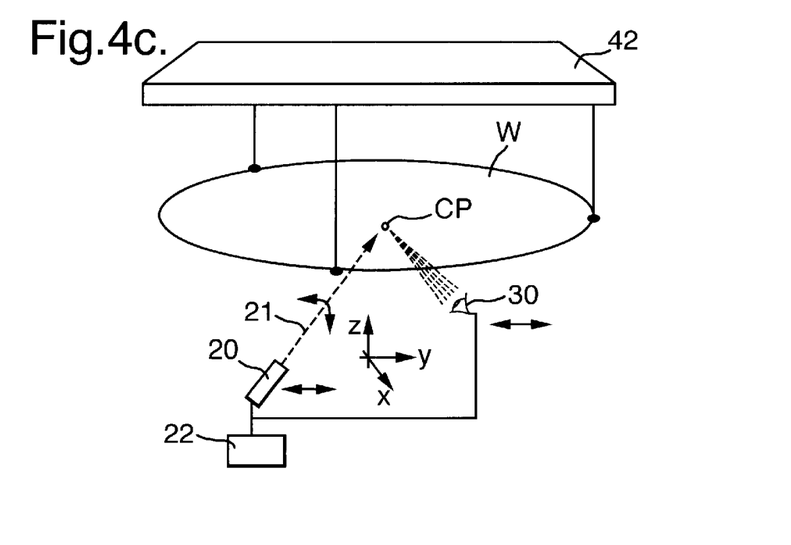

FIGS. 4a, 4b and 4c show contamination detection means according to a fourth embodiment of the invention. Said contamination detection means may comprise an inspection tool that may be used to inspect for contamination being present on the backside surface of a substrate W. In case contamination CP is detected the substrate W will be rejected and not loaded into the apparatus. Contamination CP is thus prevented from entering the lithographic apparatus and coming in between the support surface WH and the substrate W, and possibly remaining on the support surface WH when the substrate W is unloaded from the substrate table WT.

The inspection tool comprises a light source such as a laser 20 in the tools shown. The laser beam 21 from the laser is directed onto and will specularly reflect from the backside surface of the substrate W. However, any contamination particle CP present on the backside will scatter a fraction of the laser beam 21 in all directions, which scattered light is detected by a detector 30 positioned off-specular. In operation the substrate W is loaded into the inspection tool and the laser beam 21 is scanned over the backside surface of the substrate, the detector 30 and associated electronics yielding a signal pulse when a contamination particle CP is encountered by the laser beam 21. The substrate W may than be rejected from entering into the lithographic apparatus and being loaded onto the substrate table WT. A rejected substrate may be put into a special carrier.

FIGS. 4a, 4b and 4c show three different embodiments for the substrate backside inspection tool. In the FIG. 4a inspection tool the substrate W is to be placed on a rotation unit 41 of the inspection tool for supporting and rotating the substrate W. In operation the laser beam 21 is scanned back-and-forth in a radial direction x over the backside surface of the substrate W by a laser scanning unit 22 as the substrate is rotated by the rotation unit 41.

In the inspection tool shown in FIG. 4b the substrate W is held by three supports on a supporting unit 42 of the inspection tool. The laser beam 21 is scanned back-and-forth by a laser scanning unit 22 in a first direction x over the backside surface of the substrate W while the substrate is translated by its supporting unit 42 in a second direction y which is orthogonal to the first direction x.

The FIG. 4c inspection tool comprises a supporting unit 42 having three supports for supporting the substrate W, and a laser scanning unit 22 providing for scanning of the laser beam 21 back-and-forth over the backside surface in a first direction x and in a second direction y which is orthogonal to the first direction. The detector 30 is in the third inspection tool mechanically or electrically coupled to the laser scanning unit 22 to displace the detector 30 in the direction y in synchronization with the y-movement of the laser 20.

Scanning of the laser in the various inspection tools may be obtained by translation of the laser, a suitable rotational movement of the laser and/or deflection of the laser beam by a movable and/or rotatable mirror.

The inspection tool may be incorporated in a substrate handling unit positioned next to the imaging part of the lithographic apparatus. The handling unit takes the substrates from a special track delivering the substrates to the apparatus or from a carrier in which several substrates are stored, inspects the substrates for contamination, puts the rejected substrates in special carrier, and hands clean substrates over to and takes exposed substrates from the imaging part of the apparatus to deliver them to another track or another carrier for storage.

While specific embodiments of the invention are disclosed above it will be appreciated that the invention may be practiced other than described. For example, the invention may be used to detect contamination present on a mask and/or mask holder.

What is claimed is:

1. A lithographic projection apparatus comprising:
   an illumination system constructed and arranged to supply a projection beam of radiation;
   a first object table for holding a mask;
   a second object table provided with a support surface constructed and arranged to supply and hold a substrate at a backside surface of the substrate;
   a projection system constructed and arranged to image an irradiated portion of the mask onto a target portion of the substrate; and
   a contamination detector constructed and arranged to detect the presence of contamination on one or both of the support surface and the substrate backside surface;
   wherein said contamination detection means comprises:
      a level sensor constructed and arranged to detect a surface figure of a substrate positioned upon said support surface;
      a data storage for storing surface figures of at least two substrates; and
      a processor adapted to compare surface figures of at least two substrates stored in said data storage so as to recognize a recurring deformation in the surface figures of said substrates at a similar location indicating the presence of contamination at that location on said support surface,
      said contamination detector adapted to detect a location of contamination on said support surface; and
      a cleaning tool adapted to move with respect to said support surface to said location and to clean said location.

2. Apparatus according to claim 1, wherein said cleaning tool comprises a cleaning block having a cleaning surface and is further constructed and arranged to be positioned with its cleaning surface against said support surface and to be movable with respect and parallel to said support surface when positioned against said support device.

3. Apparatus according to claim 2, wherein the cleaning block comprises a ceramic material.

4. Apparatus according to claim 3, wherein the ceramic material is selected from the group comprising alumina and titanium oxide.

5. Apparatus according to claim 2, wherein the cleaning block is at least partially electrically conductive.

6. Apparatus according to claim 2, wherein the cleaning surface of the cleaning block has a surface roughness of 0.1 $\mu$m or less.

7. Apparatus according to claim 2, wherein said cleaning block comprises a sponge.

8. Apparatus according to claim 7, wherein said sponge is constructed and arranged to be provided with a solvent.

9. Apparatus according to claim 1, wherein said cleaning tool comprises a source of radiation and a radiation director constructed and arranged to direct said radiation onto said support surface to clean said support surface.

10. Apparatus according to claim 9, wherein said radiation comprises ultra-violet radiation.

11. Apparatus according to 9, wherein said cleaning tool further comprises a purge gas supply constructed and arranged to supply a purge gas over said support surface.

12. Apparatus according to claim 1, wherein the contamination detector comprises a substrate inspection tool constructed and arranged to inspect the backside surface of the substrate for contamination and to reject a contaminated substrate from being loaded onto the support surface.

13. Apparatus according to claim 12, wherein said inspection tool comprises a radiation source generating a beam of electromagnetic radiation, means constructed and scannable over the backside surface of the substrate, and a detector constructed and arranged to detect radiation which is off-specularly scattered by contamination present on said backside.

14. A device manufacturing method comprising:
   providing a substrate which is at least partially covered by a layer of radiation-sensitive material to a substrate table provided with a support surface, for holding and supporting the substrate at its backside;
   providing a mask which contains a pattern;
   using a projection beam of radiation to project an image of at least a portion of the mask pattern via a projection system onto a target portion of the layer of radiation-sensitive material;
   detecting the presence of contamination on one or both of the support surface and the substrate backside surface, said detecting comprising sensing a surface figure of the substrate, storing respective surface figures of at least two substrates, and comparing the surface figures of the at least two substrates so as to recognize a recurring deformation in the surface figures of the substrates at a similar location thereon, indicating the presence of contamination at that location on the support surface; and
   responsive to the detecting, cleaning the location on the support surface.

* * * * *